United States Patent [19]
Sebastian et al.

[11] Patent Number: 5,416,321
[45] Date of Patent: May 16, 1995

[54] INTEGRATED APPARATUS FOR MAPPING AND CHARACTERIZING THE CHEMICAL COMPOSITION OF SURFACES

[75] Inventors: Richard L. Sebastian, Mason Neck; Buddy G. Beck, Fairfax Station, both of Va.

[73] Assignee: Coleman Research Corporation, Fairfax, Va.

[21] Appl. No.: 43,722

[22] Filed: Apr. 8, 1993

[51] Int. Cl.⁶ .................. B01D 59/44; H01J 49/00; G01C 3/00
[52] U.S. Cl. ..................... 250/288; 356/4.01
[58] Field of Search ............ 250/281, 288, 288 A; 356/2, 4.5

[56] References Cited

U.S. PATENT DOCUMENTS

| | | |
|---|---|---|
| 4,281,876 | 8/1981 | Lansberry . |
| 4,282,511 | 8/1981 | Southgate et al. . |
| 4,294,544 | 10/1981 | Altschuler et al. . |
| 4,344,146 | 8/1982 | Davis, Jr. et al. . |
| 4,526,311 | 7/1985 | Schröder . |
| 4,594,000 | 6/1986 | Falk et al. ............... 356/5 |
| 4,611,912 | 9/1986 | Falk et al. ............... 356/5 |
| 4,620,285 | 10/1986 | Perdue . |
| 4,652,204 | 3/1987 | Arnett . |
| 4,674,048 | 6/1987 | Okumura . |
| 4,706,120 | 11/1987 | Slaughter et al. . |
| 4,709,265 | 11/1987 | Silverman et al. . |
| 4,714,339 | 12/1987 | Lau et al. ............... 356/4.5 |
| 4,727,179 | 2/1988 | Schmalfuss . |
| 4,746,977 | 5/1988 | White . |
| 4,881,177 | 11/1989 | McClean et al. . |
| 5,086,535 | 2/1992 | Grossmeyer et al. . |
| 5,098,451 | 3/1992 | Rounbehler et al. . |
| 5,108,705 | 4/1992 | Rounbehler et al. . |
| 5,114,226 | 5/1992 | Goodwin et al. ............... 356/4.5 |
| 5,123,274 | 6/1992 | Carroll et al. . |
| 5,147,002 | 9/1992 | Hughes . |
| 5,182,641 | 1/1993 | Diner et al. . |

FOREIGN PATENT DOCUMENTS

WO91/08466  6/1991  WIPO .

*Primary Examiner*—Bruce C. Anderson
*Attorney, Agent, or Firm*—Millen, White, Zelano, & Branigan

[57] ABSTRACT

An apparatus which accurately maps and detects contaminants within interior surfaces is provided. The apparatus finds use in supporting decontamination operations by providing on-site chemical analyses defining the condition of contaminated areas and monitoring the progress of clean-up operations. An optical vision system is used to accurately map the surface to be investigated or treated as a reference. Analytical probes are used to sample the mapped surface to detect inorganic and organic contaminants in situ. Automated controls which manipulate the analytical probes and high speed analytical equipment, such as a high speed gas chromatograph, are optionally used to take large numbers of samples quickly and remotely. The optical vision system tracks the position of the analytical probes, providing an accurate map of the location of the contaminants. The precise positioning of the contaminants and ease of sampling allows for more accurate characterization of the surfaces before, after, and during clean-up operations. The real-time analysis of the inspection sites also eliminates unnecessary and wasteful clean-up activity.

38 Claims, 4 Drawing Sheets

INTEGRATED APPARATUS FOR MAPPING AND CHARACTERIZING THE CHEMICAL COMPOSITION OF SURFACES

FIELD OF THE INVENTION

The present invention relates to apparatus which both maps and characterizes the chemical composition of surfaces to support clean-up (decontamination and decommissioning) operations. More particularly, the present invention relates to apparatus which is capable of in situ detection and mapping of inorganic and organic surface contaminants on-site.

BACKGROUND OF THE INVENTION

Accurate physical characterizations of surfaces for radioactive and organic contamination on and beneath the surfaces is a critical part of decontamination and decommissioning operations such as those by the Department of Energy. Present methods for detecting contaminants within a manufacturing, storage, transport, or other facility involve the manual collection of samples for off-site conventional laboratory analysis. Due to potential exposure to contaminants, workers must protect against unknown risks, e.g., through the use of protective clothing. The collected samples must be treated with caution because of the potential for contamination; samples must be carefully sealed and stored for transport to an off-site laboratory for analysis. While actual analyses for inorganic and organic contaminants, such as gas chromatography, mass spectrometry, infrared spectrometry, are typically performed relatively quickly, it takes a number of days to obtain results due to the handling, storage, and transport of the samples. These delays do not allow for a rapid determination of the progress of clean-up operations. Therefore, rapid adjustment of a clean-up strategy is not possible. Due to the slow response time, remediation activities can continue beyond the point of compliance, resulting in the superfluous removal of otherwise clean material.

Another disadvantage of collecting samples manually involves the accurate characterization and mapping of a surface for contaminants. Precise positioning of the sample source is difficult due to limitations on the means by which the samples are taken. In addition, collecting and archiving the data requires manual input and is subject to human error. The extensive effort required to obtain and analyze samples manually does not encourage redundancy to improve the reliability of the data.

It is desirable to provide an apparatus which offers a prompt, real-time analysis of surfaces for contaminants during clean-up operations so that compliance with standards and regulations can be determined quickly, and resources for clean-up operations can be used more effectively without generating unnecessary waste. In addition, it is desirable to automate sampling of the environment to eliminate exposure by workers and laboratory personnel to contaminants, thereby reducing health and safety risks. There is also a continual effort to improve the accuracy of characterizing and mapping surfaces for contaminants, since improved reliability of the data results in greater regulatory confidence.

SUMMARY OF THE INVENTION

It is an object of the present invention to provide an apparatus for sampling, mapping, and characterizing the chemical composition of a surface which is more efficient and accurate than manual sampling methods.

It is another object of the present invention to provide an apparatus for mapping and characterizing the chemical composition of surfaces which functions on-site.

It is a further object of the present invention to provide an apparatus which quickly maps and characterizes surfaces for contaminants so that compliance with standards can rapidly be determined, reducing unnecessary, wasteful clean-up activity.

It is yet another object of the present invention to provide an apparatus for the mapping and characterization of surfaces for contaminants which easily and accurately archives the data obtained.

Upon further study of the specification and appended claims, further objects and advantages of this invention will become apparent to those skilled in the art.

These and other objects are achieved with the apparatus of the present invention, which provides for the integrated mapping and characterization of surfaces for chemical composition in situ, including the in situ detection of contaminants both on and beneath surfaces. The preferred apparatus comprises two, preferably mobile, platforms: one supporting a multisensor head with position and analytical sensors and another supporting an optical vision system which topographically maps the surface to be characterized and helps position the multisensor head over the surface. The apparatus also comprises at least one workstation, preferably remote from the platforms, which controls the optical vision system and multisensor head and also collects and processes data to characterize the chemical composition at the sample locations on the surface. Where the platforms are mobile, the workstation controls their motion and position. The primary platform incorporates a scanning laser or other optical vision system which, preferably, utilizes coherent optical detection suitable for three-dimensional mapping. A secondary platform incorporates one or more analytical probes for sampling the surface for chemical analysis. Where the platforms are mobile, they comprise a transport vehicle which is preferably remotely controlled.

The apparatus of this invention more specifically comprises:

a primary platform upon which is supported an optical vision system adapted to topographically map surfaces within a target volume by directing a source light beam through the target volume, receiving the reflected source light beam from a point on a surface within the target volume, and analyzing the reflected source light beam to provide a locus for a topographical map, said optical vision system having means for scanning the source light beam through multiple points within the target volume;

a secondary platform upon which is supported a multisensor head and means for manipulating the position of the multisensor head over the mapped surface within the target volume, the multisensor head comprising at least one analytical probe connected to a remote detector which samples portions of the mapped surfaces within the target volume for chemical analysis;

a remote detector which, together with an analytical probe, performs chemical analysis in situ on the sample portions of the mapped surfaces within the target volume; and one or more workstations with data processing means which:

controls the means for scanning the source light beam through multiple points within the target volume, monitors the position of the multisensor head within the target volume from input by the optical vision system, controls the means for manipulating the position of the multisensor head over the mapped surfaces within the target volume, correlates data from the remote detector and analytical probe with data from the optical vision system, and reports the results of the chemical analysis of the sample portions and the locations of the sample portions on the mapped surfaces.

The present invention performs fast, accurate surface characterizations, resulting in efficient clean-up operations, less waste generation, and reduced human exposure to hazardous conditions when compared to manual sampling. On-site testing eliminates the extensive sample handling associated with off-site analysis and storage, improves the reliability of the data, and significantly reduces sample preparation time and cost. Sample points can be precisely laser-located up to within 1 mm. Computer recording capability of the sample location eliminates human error. The automatically archived characterization data results in greater reliability in the data and greater regulatory confidence.

In characterizing the chemical composition of surfaces, the apparatus of the present invention is capable of detecting organic and inorganic contaminants. Such measurements can be obtained in real-time, and the contaminants can be detected in situ.

Real-time operations significantly advance analytical capabilities beyond present levels. For example, mapping immediately clarifies areas of both high and low risk, and on-site chemical analysis will provide means to measure progress and modify clean-up strategy immediately. On-site real-time analysis also provides quick response time for engineers to minimize environmental damage. Manpower and equipment costs are also reduced because of the availability of real-time data. Compliance with federal, state, and local regulations can be determined intermittently to prevent the performance of clean-up operations on clean surfaces. Furthermore, by halting operations as soon as compliance is achieved, the removal of otherwise clean material is prevented. Analysts will also be able to classify materials as they are removed so as to optimize clean-up operations in a manner consistent with the hazard level.

The simplicity of in situ analysis improves the effectiveness of the response at identified sites by streamlining the entire process of site analysis, from beginning to end, i.e., from the initial contamination survey through monitoring of the progress of site restoration efforts and determining when regulatory standards have been met. A large number of samples can easily be obtained to better characterize the surfaces to be analyzed.

DETAILED DESCRIPTION OF THE PREFERRED EMBODIMENTS

The apparatus of the present invention comprises two platforms, each preferably mobile. A primary platform, also referred to herein as a "mapper platform", supports an optical vision system adapted to topographically map surfaces within a target volume, wherein a source light beam is directed at a surface within a target volume, and the light beam reflected from the surface is received and analyzed to provide a locus on said topographic map. A second platform, also referred to herein as a "sensor platform", supports a multisensor head which includes at least one analytical probe connected to a remote detector which samples portions of the surface for chemical analysis, and, optionally, a surface proximity sensor and/or a light sensor. The remote detector may also be supported by the secondary platform. The multisensor head is mobile, and its position within the target volume is monitored and controlled with the aid of the optical vision system, and, optionally, a surface proximity sensor. One or more integrated workstations process and correlate the information obtained from the one or more analytical probes and remote detectors with information obtained from the optical vision system and report the results of the chemical analyses of the surface samples with their location on the mapped surface.

The critical feature of the present invention is the capability to map the physical environment to be characterized and to automatically monitor and control the location of samples taken from within that environment. This function is dependent on the mapping platform and the optical vision system incorporated therein. Conventional optical vision systems can be used for this purpose. Those which are preferred provide high resolution (low range error) at far ranges; utilize compact, simple architecture; and can be focused automatically. Systems which provide 1 mm resolution at a range of 5 M or more preferred.

The optical vision system preferably has a range of more than 5 m, more preferably beyond 15 m, and most preferably up to and beyond 30 m with 1 mm resolution. The longer ranges are desired so that the primary platform need not be repositioned when mapping large surface areas. High resolution is desired in that it allows the apparatus to more accurately compute the amount of contaminant material removed during clean-up operations when comparing pre- and post-decontamination maps. It is also preferable that the optical vision system provide three-dimensional mapping capability to allow for mapping of surfaces in different planes, such as walls and ceilings or walls and tables.

Figure 1:
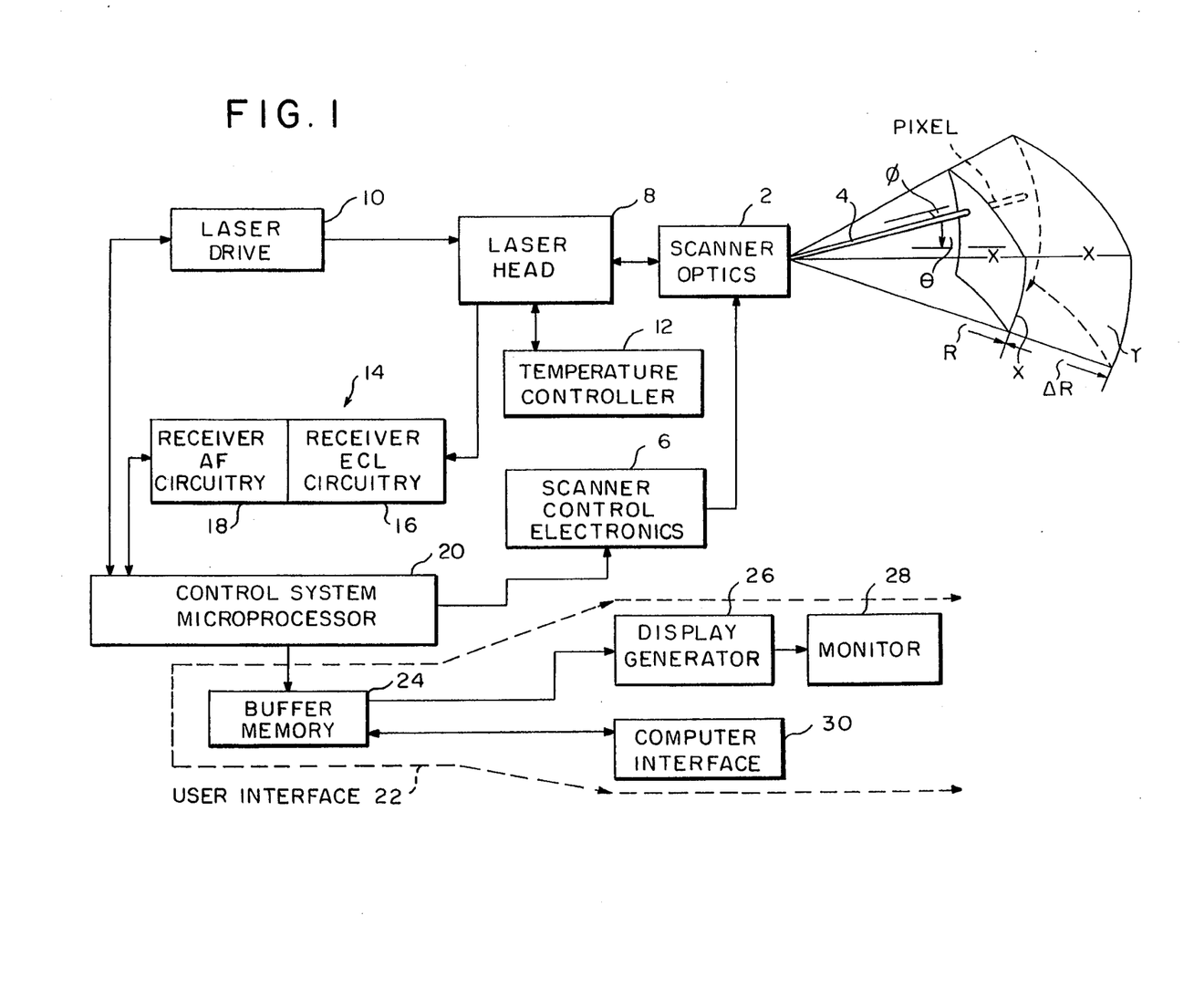
FIG. 1 is a schematic representation of an optical vision system suitable for use in this invention.

FIG. 1 illustrates the basic components of an optical vision system suitable for use in this invention. The three-dimensional target is defined by curved surfaces x and y, and the range resolution of the system, $\Delta R$, thus provides a target volume Z from which information may be derived. Scanner optics 2 scans a light source beam 4 through the target volume Z. A source light beam scans the target volume 1 pixel at a time. The scanner optics 2 is controlled by scanner control electronics 6 to scan source light beam 4 through the target volume utilizing changes in azimuth angle $\phi$ and elevation angle $\theta$. Those of skill in this field will recognize that a variety of mechanical and electronic scanning devices and techniques may be utilized within the scope of the present invention. For example, a serpentine scan pattern or raster scan pattern provided by a motor-drive facet wheel may be used.

A laser head 8 provides the optical source light beam to scanner optics 2. The laser head 8 is driven by a laser drive 10, which acts to modulate the source light beam. In a preferred embodiment, the laser drive 10 provides frequency modulation to the source light beam. A temperature controller 12 acts to stabilize the laser head 8 to provide a stable source light beam.

After reflection from the surface, the return light beam passes back through the laser head 8 to receiver circuitry 14. The receiver circuitry 14 may include receiver ECL circuitry 16, and receiver RF circuitry 18. The structure and function of such circuitry are known in the field and will not be described in detail. This combination of ECL and RF circuitry provides a compact and efficient subsystem for processing the received signal. A workstation microprocessor 20 acts to control the system and to output usable signals to user interface subsystem 22. Such a microprocessor and user interface are part of a workstation (not shown). The workstation microprocessor 20 thus controls the scanning of the light source beam through standard control electronics 6. The workstation microprocessor 20 also controls the laser driver 10 to provide appropriate modulation through the source light beam. The microprocessor also acts to control receiver circuitry 14, to receive output signals therefrom, and to output usable signals to a user interface, including a buffer memory 24.

A wide variety of equipment may be employed in the user interface. For example, a display generator 26 may provide image data to a monitor 28. Likewise, computer interface 30 may be coupled to buffer memory 24 so that usable signals may be provided to a further processing system, such as a robot controller.

While a number of vision systems can perform the mapping function, a preferred optical vision system is that which utilizes coherent optical detection, such as is described in U.S. Pat. No. 5,114,226. Those systems which are based on fiber optics are particularly preferred. This system provides three-dimensional mapping through the use of a frequency-modulated coherent (diode) laser. This system is referred to herein as "FM coherent laser radar 3D mapper". This system provides speed and accuracy advantages over alternative three-dimensional mapping systems which are suitable, such as amplitude-modulated (AM) laser and structured light systems. The speed and accuracy advantages over AM laser radar are the result of the enormous optical modulation bandwidth ($\Delta f \approx 200$ GHz) for FM systems, compared to the lesser modulation bandwidth ($\Delta f \approx 5$ Ghz) of AM systems. The AM systems utilize substantially the same architecture; however, they do not modulate the lightwave frequency but instead modulate an AM carrier tone. The advantages derived from the broader bandwidth are illustrated directly by the equation for range measurement error ($\sigma_R$), which applies to both AM and FM systems:

$$\sigma_R = \frac{\sqrt{3} \, C}{2\pi (\Delta f) T^{\frac{1}{2}} (S/N_o)^{\frac{1}{2}}}$$

wherein:
f is frequency,
T is time,
C is the speed of light, and
$S/N_o$ is the signal-to-noise ratio (Hz).

From this equation, it is seen that the average range error is inversely proportional to the modulation bandwidth. It is also seen that for a given accuracy and measurement error, the measurement time T is proportional to $1/\Delta f^2$. A dwell time for the FM coherent laser radar 3D mapper of 0.5 msec is accurate to about 10 $\mu$m, and, for a dwell time of 2 msec, the system is accurate to about 5 $\mu$m.

The coherent laser radar systems have advantages over structured light systems, which work by triangulation between the laser source in a first position, a detector in a second position, and a target point on the surface being mapped. At close range, this method can yield acceptable $\pm 1$ mm range errors. At longer ranges of 5 M or more, however, the limited emitter-detector spacing on a single platform will yield range measurement errors in several centimeters. These range limits make coherent laser radar systems more desirable. Long ranges are desired to minimize the need to reposition the optical vision system to view large surfaces. Measurement accuracy integrity is lost by this process because it is dependent on the positioning accuracy of the platform.

The FM coherent laser radar 3D mapper also has advantages over AM laser systems in that it is immune to ambient light and surface shading. Immunity to lighting conditions means that clean-up operations will not have to be disrupted while lighting is controlled for mapping operations.

Figure 4:
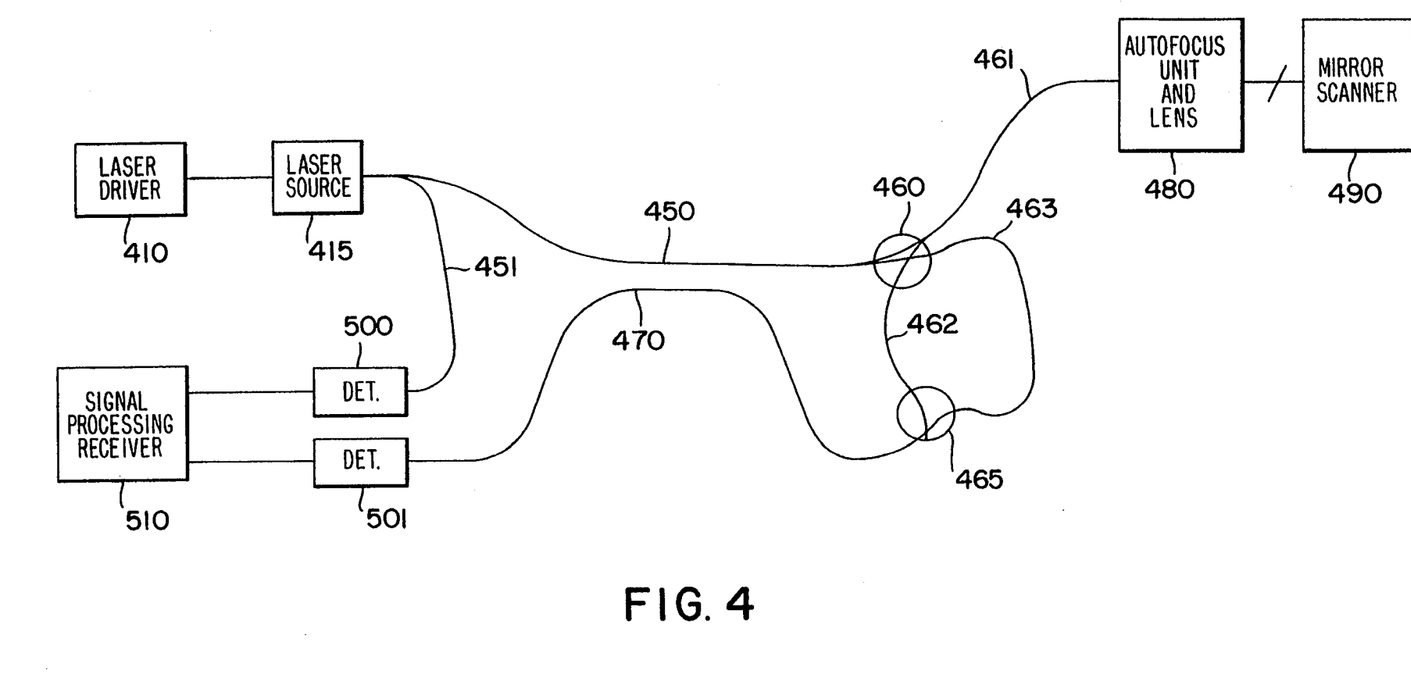
FIG. 4 is a schematic representation of an optical vision system based on fiber optics suitable for use in this invention.

Another feature desired in the optical vision system is the availability of compact, simple equipment. FM coherent laser radar 3D mapper systems provide such a feature in that they can be implemented with lightweight, radiation-resistant fiber optics. This allows for a remote scanner with no solid-state electronics positioned in a contaminated site. The remote scanner can be positioned on the primary platform kilometers away from the workstation if desired. Multiple FM coherent laser radar 3D mapper systems can be controlled by a remote workstation with conventional electronics and data processors. FIG. 4 schematically illustrates a configuration of an FM coherent laser radar optics system which implements fiber optics. Laser drive 410 drives laser source 415, which transmits a source beam through fiber cable 450 and a reference beam through fiber cable 451 to detector 500. Fiber optic coupler 460 splits the light into the measurement path via fiber cable 461 and local oscillator path via fiber cable 463, which is preferably switchable (not shown). Light from cable 461 is focused by autofocus unit and lens 480 and scanned by mirror scanner 490. Reflected light is transmitted through mirror scanner 490, autofocus unit and lens 480, fiber cable 461 to fiber optic coupler 460. Fiber cable 463 transmits the local oscillator beam to fiber optic coupler 465. The reflected light is also transmitted to fiber optic coupler 465 via fiber cable 462. The reflected light and local oscillator beam are both transmitted to a detector 501 via fiber cable 470. Signal processing receiver 510 extracts information from the reflected light.

Preferred components of an FM coherent laser radar 3D mapping system which contribute to accuracy and range include the use of a wide tuning, narrow linewidth laser diode such as that provided by GEC Marconi under the designation Model LD 5171. Another preferred component is a variable delay local oscillator. Other preferred components of an FM coherent laser radar 3D mapper system are mentioned in U.S. Pat. No. 5,114,226, such as the use of retroreflector means, which reduces the sensitivity of the mapper system to misalignment of components such as the detector and beam splitter. Most preferably, the laser system is based on fiber optics which do not require many of the components shown in FIG. 3 to generate an oscillator beam for comparison to a reflected beam. Preferably, the beam splitter and retroreflecting prism can be eliminated. Therefore, the fiber optic based FM coherent laser radar mapper system can be focused automatically by manipulation of only the scanner optics. Autofocus systems well known in the art can be used to accomplish this purpose.

By integrating an accurate mapping capability with the sampling and testing of surfaces, robotics operations can proceed with less supervision for characterization, decontamination, and dismantling operations. For example, clear visualization of the surface provided by the FM coherent laser radar 3D mapper system allows for more accurate location of surface contaminants, allows sensor probes to follow closely to the surface to be tested without collision, and provides better shape and surface texture determinations for contaminant penetration modeling. In addition, clear visualization of the surface can provide information which will allow object recognition, material recognition, and scene combing with the appropriate software and data processing equipment.

The optical vision system includes means for manipulating the direction of the source light beam to pass through multiple points within the target volume. With an FM coherent laser radar system, conventional scanner optics are suitable. Although not critical to the accuracy of the system, it is desirable for the optical visual system to make a number of measurements within a short period of time when generating a map. Scanning rates of 10,000 measurements per second are desired. Scanning rates far less, such as 1000 per second, are suitable, however, and such rates can be obtained with conventional optical vision systems.

The apparatus of this invention also incorporates a secondary platform which supports a multisensor head. Means for manipulating the position of the multisensor head is required to sweep the mapped surfaces for characterization. Such means can vary widely in configuration and function. Where such surfaces are simple in configuration, means for manipulating the position need not be complex. A remote-controlled robot arm is preferred, particularly where the second platform is mobile. The robot arm can provide great range of movement in three dimensions and is desirable where the mapped surfaces lie on more than one plane. The configuration and operation of the robot arm can vary widely, but conventional devices can be used in the apparatus of this invention. Stability of the manipulating means, such as the robot arm, and the time to achieve stability after movement from one position to another are key issues in determining whether the manipulating means are suitable. Preferably, positioning time is less than 10 seconds to facilitate the taking of a number of samples.

The multisensor head may optionally comprise reflector means, such as a passive retroreflector for reflecting the source light beam emitted from the optical vision system of the primary platform or a light sensor which detects the light emitted from the optical vision system. The reflector means or light sensor aids in tracking the multisensor head as it is moved over the mapped surface.

The multisensor head optionally comprises one or more surface proximity sensors for determining the distance of the multisensor head to the mapped surface to be characterized. For some embodiments, these sensors may be required to avoid contact with the surface and the consequential cross-contamination of samples. Conventional proximity sensors, such as the acoustic type or those which implement a laser with fiber optics, can be utilized for this purpose.

The multisensor head incorporates one or more analytical probes connected to a remote detector for sampling the mapped surface for chemical analysis. Preferably, the analytical probe samples an area of from 1 $mm^2$ to 1 $cm^2$. The chemical components are analyzed in situ by the probe/detector combination without removal of materials from the surface. Suitable probe/detector combinations include those which perform one or more of the following analytical processes: gas chromatography, mass spectrometry, molecular vibrational spectrometry, radio nuclide analysis, and the like. Preferably, the analyses associated with these probe/detector combinations can be performed quickly so as to facilitate repositioning of the multisensor head for further sampling. The probe/detector combination can provide the data necessary for analysis in a number of ways through data and/or fiber optic cables. A workstation processes data from the detector and reports the results of the chemical analysis with the location of the sample on the mapped surface. Preferably, the workstation archives these results, as well.

The detectors connected to the analytical probes are positioned remotely from the multisensor head. They may be positioned on the secondary platform or remote from the secondary platform. Where the detector incorporates complex electronics, it is preferable to maintain the detector remote from the site of the mapped surface.

The apparatus of the present invention also incorporates one or more workstations which perform many functions, including controlling the means for manipulating the position of the source light beam to define the target volume. The workstations also monitor the position of the multisensor head within the target volume and control the position of the multisensor head with input from the optical vision system and, optionally, a surface proximity sensor and/or a light sensor. The one or more workstations report the results from the chemical analysis of the sample portions performed by the detectors with the location of the sample portions on the mapped surface. Preferably, this information is stored/archived by the one or more workstations. Where the primary and secondary platforms are mobile, the workstation also incorporates means for determining the position of each platform and for controlling its movement.

The control functions and data processing performed by the workstation can be accomplished with conventional data processing equipment. Those skilled in the art can easily adapt and program such conventional equipment to perform the required tasks.

The workstations are preferably remote from the area to be tested to isolate the electronic components therein from potential contaminants and, therefore, are preferably remote from the primary and secondary platforms. The primary and secondary platforms can be connected to the one or more remote workstations via conventional data cables, fiber optic cables, and/or power cables.

As discussed above, the primary and secondary platforms may be mobile; and, where so, they preferably incorporate separate transport vehicles. It is contemplated that there may be some applications where one transport vehicle can be used for both platforms; however, the performance of the optical vision system may be hindered because of instability caused by the motion of the multisensor head and the long distances which may be necessary between the optical vision system and the multisensor head.

The transport vehicles can be conventional robotic platforms capable of negotiating corridors, stairways, closets, etc. An example of a suitable transport vehicle is the "Andros Robot", available from Remotec of Oak Ridge, Tenn. Conventional mobile platforms have reels which can manage a control/data tether and can operate at up to 500 feet from a workstation without modification. Radiowave-controlled transport vehicles are also suitable. To control the remote vehicles, robotic programs for the Department of Defense involving navigation, sensing, and control can be utilized. Where the primary and secondary platforms are mobile, it is preferable for each to incorporate a video camera for remote, real-time viewing to aid in remotely directing the platform.

Figure 2:
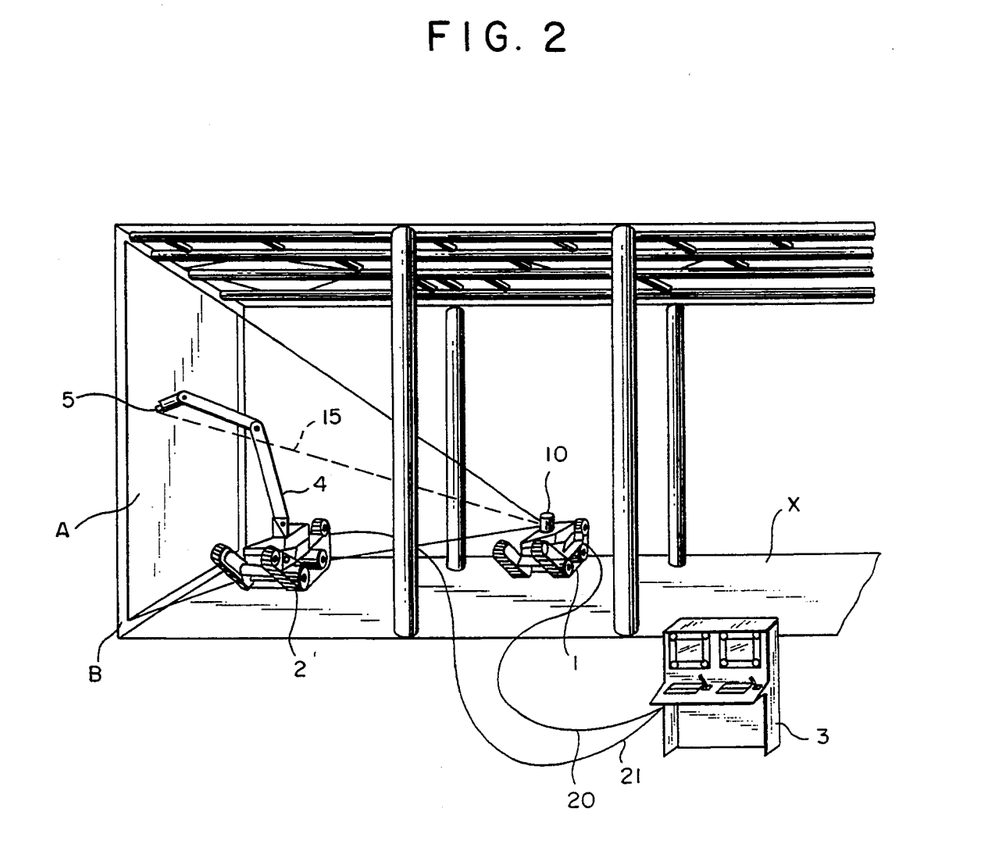
FIG. 2 is a perspective view of an embodiment of this invention in operation.

FIG. 2 illustrates an embodiment of this invention, wherein a primary platform 201 and a secondary platform 202 are mobile and are positioned in test area X. The primary and secondary platforms are controlled by a workstation 203 via control/data cables 220 and 221, respectively. A robotic arm 204 manipulates the position of a multisensor probe 205. A laser 210 of an optical vision system is positioned on the primary platform 201 and defines a target area A on a surface B. A source light beam 215 from the laser 210 is shown tracking the multisensor probe 205.

The preferred apparatus of this invention functions as follows: The mapper platform is first positioned in a room selected for characterization. Where the mapper platform is mobile, the operator at a workstation remotely drives the platform into the room. At this stage, the operator plans and directs the selection of surface areas to be characterized and the density of samples to be employed. Three-dimensional mapping of the surfaces to be tested in the inspection area is initiated. The mapper platform determines and maintains its precise location as the optical vision system scans a target volume with a source light beam to topographically map surfaces therein. The sensor platform is then positioned in the room. The robot arm on the sensor platform automatically moves the multisensor head to successive sample locations within the target volume under the remote observation of the optical vision system positioned on the mapper platform and control of the workstation. A surface proximity sensor on the multisensor head may be used to assist in the task of avoiding contact with the surface and consequential cross-contamination of samples. Positioning of the multisensor head may be accomplished without surface contact by first moving the multisensor head into the desired location at coordinates parallel to the surface and rotating the multisensor head to the proper orientation with respect to the surface. Final positioning may require some adjustment.

Once the robot arm has stabilized, one or more analytical probes on the multisensor head sample the surface for the analysis of chemical components in situ. Radio nuclide analysis is determined by a conventional Geiger counter ($\alpha/\beta$-detector). Fiber optics provide means for radiating the surface with light and obtaining spectral analysis. In obtaining samples for GC analysis and mass spectrometry, the surface is locally heated to withdraw vapors which are transported to a GC analyzer and/or mass spectrometer. When the samples are obtained, the multisensor head may be moved to another location. The analyte may be simultaneously processed during repositioning.

In a preferred process, chemical analysis identifies the base material, and the level of contaminants of interest is determined with the aid of the one or more workstations. The data from chemical analysis and the surface map location are archived, allowing for easy regulatory review; and the dense, uniform surface sampling allows for straightforward establishment of contoured bounds of regions exceeding regulatory limits. Base material identification and contamination level data from the analytical probes are displayed on a physical map as the optical vision system continually tracks the location of the multisensor head.

The separation of the sensor and mapper platforms allows the sensor platform to reach all of the required characterization surfaces, while the mapper monitors the position of the multisensor probe unperturbed by the motion of the sensor platform or its robot arm.

Coherent Laser Radar

As discussed above, preferred vision systems utilize coherent optical detection. Such systems are described by Falk et al. in U.S. Pat. Nos. 4,594,000 and 4,611,912 and Goodwin et al. in U.S. Pat. No. 5,114,226 and in the article entitled, "Coherent Optical Detection: A Thousand Calls on One Circuit," by Link and Henry, IEEE Spectrum, February 1987, pp. 52–57. These optical detection systems provide high precision and short dwell times at relatively long target distances. The preferred coherent optical vision system used in the present invention utilizes a frequency-modulated optical source, which produces a continuous beam of radiation directed at a target surface. In these systems, a local oscillator beam is derived from the source light beam and is directed to a photodetector, preferably a PIN diode. Light reflected from the target surface is also directed to the photodetector. The detector sees energy reflected from the target surface, as well as directly from the source, and interference beats are detected as the frequency is swept over the interval $\Delta f$. The rate of these beats is a function of the range (as well as the magnitude of the frequency interval).

In the apparatus described in U.S. Pat. No. 5,114,226, a quarter-wave retardation plate is positioned between the target surfaces and the beam splitter, which converts the linearly polarized source light beam to right-hand circularly polarized indicator beam. This light beam is reflected from the target, reverses polarization, and is returned as a return light beam. The return light beam passes back through the quarter-wave retardation plate, where its polarization is converted. The return light beam is then reflected in the beam splitter and directed toward a secondary quarter-wave retardation plate, which again converts its polarization. This light beam is directed to a retroreflector, which again reverses the polarization of the light beam and directs it back toward the secondary quarter-wave retardation plate. The secondary retardation plate converts the light beam into the same polarization as the local oscillator beam and directs the return light beam toward the photodetector along the same optical axis as the local oscillator light beam.

The photodetector thus receives an optically mixed signal, including a local oscillator light beam and a return light beam, both having the same polarization. An output signal from the photodetector is then provided to a processor within the workstation, which derives information contained in the return light beam. Scanning means controlled by the workstation are located downbeam from the first quarter-wave retardation plate in order to scan the source light beam through the target volume and derive an image of the surfaces within the target volume.

The use of a retroreflector guarantees that the return light beam will be colinear with the local oscillator beam, thus making careful optical alignment unnecessary. It is also preferred for the FM-modulated laser diode, PIN detector, beam splitter, quarter-wave plates, and retroreflector be integrally mounted in a compact housing to eliminate any optical degradation due to temperature changes and mechanical shock.

Figure 3:
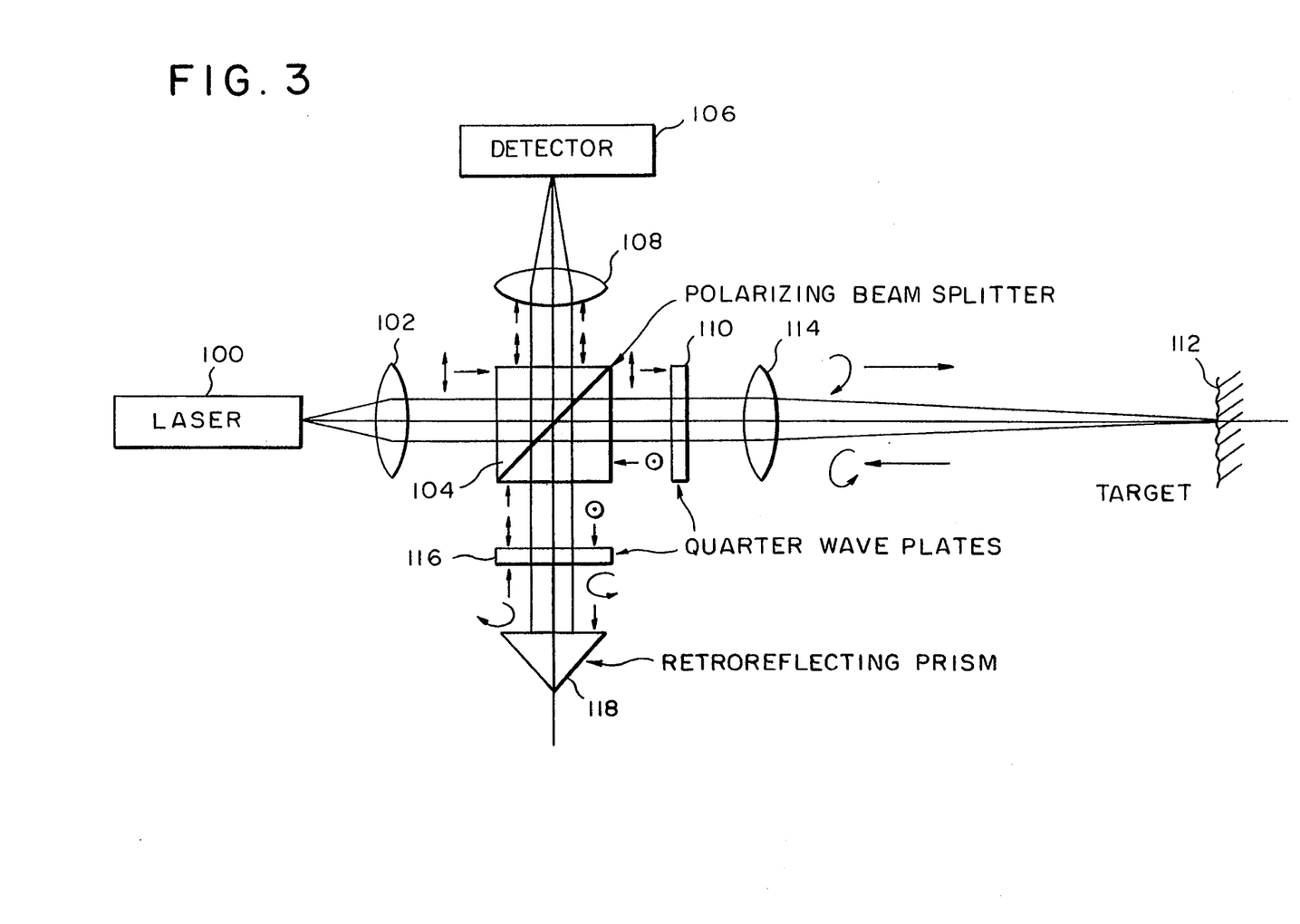
FIG. 3 is a schematic representation of an example of suitable optics for the optical vision system utilized in this invention.

An example of suitable optics for an optical vision system which utilizes coherent optical detection is shown in FIG. 3. The sensor optics of FIG. 4 are of a configuration such that alignment sensitivity in the sensor head is greatly reduced. For the optical vision systems which utilize coherent optical detection, there must be mixing between the return light beam and local oscillator beam on the deflector. Efficiency of mixing is determined by how closely matched the radii of curvature the two beams are and how well the polarizations are aligned. The configuration of FIG. 3 utilizes a local oscillator peel-off apparatus, which does not require sensitive optical adjustment and readjustment when the focus is changed. Other systems require independent optical adjustments to change of the center of focus of the signal beam.

A laser diode 100 provides a single mode, linearly polarized source light beam. For example, the light source beam may be horizontally polarized, as depicted in FIG. 3. The source light beam is collimated by a collimator lens 102. The collimated, horizontally polarized light source beam is then passed through a polarizing beam splitter 104. The local oscillator beam is generated in the polarizing beam splitter 104 due to inherent imperfections in thin-film coating dielectrics used in making polarizing prism cubes. Part of the light in the laser polarization state is reflected rather than being transmitted through the beam splitter. Thus, the horizontally polarized local oscillator beam is deflected in the polarizing beam splitter and directed toward photodetector 106 through focusing lens means 108. The signal light beam is transmitted through the polarizing beam splitter 104 toward a quarter-wave plate 110. The quarter-wave plate 110 converts the horizontally polarized light source beam into a circularly polarized light beam, for example, right-hand circular polarization.

The circularly polarized light source beam is then focused on a target 112 by focusing optics 114. The focusing optics 114 may include a single lens or a lens set, for example, a telescope. Upon reflection from the target, the circularly polarized light beam reverses the direction of circular rotation. Therefore, light reflected by the target captured by focusing optics 114 is circularly polarized in the opposite direction of the source light beam, for example, left-hand polarization. The focusing optics 114 also acts to collimate the return light beam. The collimated return light beam passes again through quarter-wave plate 110, where it is converted back to a regular polarization state perpendicular to that of the light source beam, for example, vertical polarization. Most of this light is then reflected in polarizing beam splitter 104 and directed to quarter-wave plate 116. The quarter-wave plate converts the linear polarization return light beam into a circularly polarized light beam, for example, from a vertical polarization state to a left-hand, circularly polarized light beam.

The circularly polarized light beam is then reflected by a retroreflector, for example, a retroreflecting prism 118. By placing the retroreflecting prism 118 on the same optical axis as the local oscillator light beam, the return signal will be colinear with the local oscillator beam, thus making careful optical alignment unnecessary.

The light beam reflected from the retroreflecting prism 118 is circularly polarized in the opposite rotation of the incoming light, for example, right-hand circular polarization. This return light beam again passes through quarter-wave plate 116, where it is converted to the same linear polarization state as the local oscillator beam, for example, horizontal polarization. This beam now passes through polarization beam splitter 104, where the mixing occurs. The prism interface is the point of mixing of the two beams, and, since both beams are collimated at this point and have the same polarization state, perfect mixing is ensured. The mixing thus creates a change in the optical interference pattern, which is used by the photodetector 106 to derive detailed information about the target surface. The mixed beam is imaged on the photodetector 106, which converts the optical interference pattern to an electrical signal, which can be converted to a range number understandable to the host processor.

The only critical adjustment of the optical system of FIG. 3 is the collimating laser. This can be accomplished with relative ease to a high degree of stability. Most displacement of parts is compensated for by the self-aligning properties of the retroreflector and by the single interface wave mixing on the polarization prism. It can be readily be seen that the apparatus described in FIG. 3 can be configured in a compact device and manipulated on the mapper platform. In addition, many of the components of the optic system shown in FIG. 3 can be eliminated when fiber optics are employed.

Analytical Probes and Detectors

Some of the preferred analytical probe/detector combinations utilized in the apparatus of this invention include those which perform the following analyses: gas chromatography, mass spectrometry, molecular vibrational spectrometry, and radio nuclide detection. It is preferable for these probe/detector combinations to perform analyses quickly and accurately so as not to prolong the time necessary for characterization of the mapped surfaces and to allow more samples to be taken from a given target volume. Gas chromatograph analysis of a sample with conventional analytical laboratory equipment typically requires 20-45 minutes. Such equipment is unsuitable. High speed gas chromatographs are available with significantly shorter separation times of about 100 seconds or less. Examples of high speed gas chromatographs are described in U.S. Pat. Nos. 5,098,451 to Rounbehler et al.; 5,108,705 to Rounbehler et al; 5,123,274 to Carroll et al.; and WO 91/08466 to Achter et al. These high speed gas chromatographs are adapted to function for vapors of selected compounds. By detecting selected vapors, the speed of the equipment is much faster than conventional analytical gas chromatographs used in laboratories. The high speed gas chromatograph utilized in the apparatus of the present invention is preferably adapted to handle chemical components of interest such as PCB's and the like. These high speed gas chromatograph devices preferably provide separation times of 100 seconds or less.

The analytical probes utilized with the high speed gas chromatograph will sample a surface by thermal desorption and then transport the vapors to the detector for identification and quantification, of the specific compounds desorbed. In preferred embodiments, the GC probe will thermally desorb organics from 10 $cm^2$ area of concrete to a depth of about 0.5-1 mm in less than 10 seconds. In addition, the desorbed vapors will be concentrated and transported from the desorption system to a gas chromatograph system in less than 20 seconds. It is necessary to transport the sample from the analytical probe to the detector system, which is typically about 5 M away. Preferred means for desorbing materials from the surface is an infrared lamp. A blower directs an airstream over the surface, purging desorbed materials into a collection module. The collection module consists of specifically coated materials to absorb vapors which can be separately raised to 300° C. in less than one-half second by resistive heating.

Preferably, the gas chromatograph will then separate the compounds of interest with a total elution time of from 10-30 seconds. Components of the high speed gas chromatograph critical to high speed are the small bore capillary columns, fast injectors and detectors, and high diffusivity gas carriers. Separation times are also reduced by utilizing a faster temperature programmer inlet. Temperature programmer rates as high as 1700° per second have been achieved within conventional high speed gas chromatographs which significantly reduce separation times. The performance of the high speed gas chromatograph depends on its response to the components of interest and its ability to discriminate between signals of interest and background. Commercially available detectors which may find use in this application include EGIS Explosives Detector, SENTOR Narcotics Detector, and Bruker Instruments Model No. MM-1 mobile mass spectrometer. Robbat et al., *Anal. Chem.* 1992, 64, 358–364, reports the detection of PCB's in soil with the Bruker Instruments Model No. MM-1. Erickson et al., *Anal. Chem.* 1992, 62, 1079–1084, reports the detection of gasoline range organics in combining gas chromatography with a time-of-flight mass spectrometer.

In performing mass spectrometry, it is preferable to integrate a GC apparatus, such as a high speed gas chromatograph, to separate the components in advance. A mass spectrum of the separate components eluting from the gas chromatographic column can then be obtained. Mass spectrometry provides the ability to resolve individual contaminant species. Preferably, the mass spectrometer can provide 10–20 complete mass spectra during each GC peak and can handle mass ranges for each sample of from 20–400 amu. With such capability, trace organics can be identified to levels as low as parts per billion in less than 60 seconds.

While a wide variety of mass analyzers are available, the conventional time-of-flight mass spectrometer (TOF-MS) can presently address the need for rapid analysis of the eluted samples. The TOF-MS generates pulses of ions that traverse a flight tube and arrive at the detector separated in time according to ion mass. The time-of-flight cycles require about 100 microseconds and can be repeated 10,000 times in 1 second. In operation, a very short pulse extracts ions from the ion source, accelerates them, and injects them into the flight tube. Ions are flung continuously within the ion source, and the concentration of ions builds up somewhat during the 100 microseconds between extraction pulses. A complete mass spectrum is obtained with each time-of-flight cycle. If a 100-microsecond time resolution is not needed for chromatographic peaks, a larger number of consecutive spectra are summoned. This enhances the signal-to-noise ratio and reduces the quantity of data to manageable proportions. Such time-of-flight mass spectrometer are commercially available. The sensitivity of the mass spectrometer system is determined by the rate of sample introduction. There is a trade-off between the sample introduction rate, pumping capacity, and sensitivity. The TOF-MS scan from conventional devices can achieve resolution at 400 atm units.

The multisensor head may also include a radio nuclide detection sensor so as to determine and identify radioactive species. Such equipment is commercially available and is utilized for remote detection of contaminants in nuclear facilities. A suitable device, designated as a Model 6A alpha monitor, is available from Eberline Instruments. Because of the very low penetration depth of $\alpha$- and $\beta$-particles, energy-selective $\alpha$- and $\beta$-detection can be utilized in the present invention. This is essentially a surface technique, and the information obtained relates to $\alpha$- and $\beta$-emissions per unit surface area rather than per unit volume. With a detector surface of 20 $cm^2$ emission rates of less than 1 bq/$cm^2$ can be detected in less than 1 second. This is more than sufficient to identify areas with medium to high levels of contamination. When the probe is held within 2–3 mm of the surface, the energy resolution is 0.04 MeV, which is sufficient to identify major $\alpha$-emitters such as uranium 235, uranium 238, Pu 239, Pu 242, Th 230, and other isotopes.

Another probe/detector combination which is desirable in the apparatus of the present invention is that which performs molecular vibrational spectrometry (MVS). MVS encompasses a number of spectrophotometric techniques, and a number of different probes/detectors may be used in the apparatus of this invention. MVS can be applied to recognize inorganic and organic base materials in the surface tested and also to detect moderate levels of contaminants. Preferably, such an apparatus is adapted to analyze surfaces such as metal, concrete, asbestos, and the like. In addition to characterizing surface matrix materials, MVS techniques can detect high levels of organic compounds, such as fuel oils, in inorganic matrices. This is helpful when the organic compounds may contain contaminants, such as PCB's. The system is not intrusive and does not remove material from the contaminated facility. Therefore, environmental issues relating to its use will be minimal. The MVS analytical sensor will be a fiber optic probe which radiates electromagnetic radiation and determines the response by the surface via reflected radiation. The spectrophotometric techniques and the optical techniques applied may depend on the analytes of interest. A suitable spectrophotometric technique must provide exploitable differences in the optical behavior of the contaminant to be identified in the environment tested.

Two photometric alternatives are well suited for the analysis of interior surfaces: near-infrared Raman spectrometry and mid-infrared external reflecting spectrometry. These techniques will determine the composition of inorganic construction materials, such as concrete, transite, and asbestos; synthetic polymers, such as polystyrene and polyethylene; and natural materials, such as wood, from their molecular vibrational spectra sensed through optical fibers. These techniques will also detect moderate or high concentrations of organic compounds in the inorganic matrix. With potential sample times as short as 1 second, this finds use in high speed mapping of moderate and high levels of contamination. Conventional equipment can be utilized for both near-infrared Raman spectrometry and mid-infrared spectrometry. The use of fiber optic probes in the range for near-infrared Raman spectrometry has been reported by Archibald et al., *Applied Spectroscopy*, 1988, 42, 1558. To adapt mid-IR reflectance spectrometer detectors to operate with a fiber optic probe is similarly within the skill of the art. It is recognized that other spectrophotometric alternatives are possible, including UV-visible reflectance spectrophotometry and spectrophotofluorimetry, where they can provide exploitable differences in the analytes of interest.

At wavelengths of 200-2000 $cm^{-1}$, mid-infrared spectra have strong specular reflection components, which are dependent on the surface shape and texture. However, mid-infrared spectra have the advantage of being very sensitive. Therefore, it may be desirable to utilize mid-IR spectrometry in molecular vibration bands at 2700-4000 $cm^{-1}$. It is expected that any non-metallic solid can be identified by its mid-infrared spectrum. Mid-infrared spectrometry provides a particular benefit in characterizing the O—H stretching modes of silanol on the surface of silaceous minerals and clays. These materials absorb weakly, between 3800-3500 $cm^{-1}$. The capability of measuring these bands allow asbestos, concrete, and other bulk materials to be identified. In addition, the C—H stretching modes of all organic compounds absorb in the region between about 2700-3200 $cm^{-1}$. Measurement of the mid-infrared reflectance spectrum of materials such as concrete or asbestos in this region may detect the presence of organic species down to a level of about 10 ppm. Although this may be inadequate to detect PCB's, it will detect transformer oils and may be used to quickly scan an area to determine if GC-MS measurement is necessary.

Analytical probes/detectors for near-infrared Raman spectrophotometric techniques also find use in the apparatus of this invention. Raman spectrometry involves the measurement of vibrational bands that are shifted to longer wavelengths. With a 9400 $cm^{-1}$ wave number source, for example, a 0-2000 $cm^{-1}$ vibration band is observed at 7400-9400 $cm^{-1}$, and a 2700-4000 cm vibration band is observed at 67-5400 $cm^{-1}$. The source of excitation of the Raman spectrophotometer can be used with conventional optical fibers, enabling the sample to be located hundreds of meters from the spectrometer. The preferred detector is sensitive to the upper band and will detect 0-2000 $cm^{-1}$ molecular vibrations.

Raman spectra are relatively immune to the geometry of the sample so that spectral artifacts of the type which are encountered in the mid-IR reflectance spectrometry are not observed. In addition, bands in the Raman spectra of inorganic materials below 1000 $cm^{-1}$ are strongly characteristic of their chemical composition and should permit detailed structural information to be obtained. Raman spectra achieves its highest sensitivity using short wavelength excitation, which unfortunately maximizes luminescence. Therefore, it may be preferable to utilize longer wavelengths, Nd:YAG lasers, to minimize fluorescence. Suitable FT Raman spectrometers with Nd:YAG lasers are commercially available from a number of vendors.

The multisensor probe may be configured to carry all of the above sensors or a select carrier subset. All probes may operate simultaneously, and all may be integrated. For example, an MVS sensor may be used to choose operating parameters for the GC/MS sensor. Both the molecular vibrational spectroscopy sensors and light sensors are linked via fiber optics and electronics mounted in the one or more workstations. The gas chromatography/molecular spectrometer hardware is preferably mounted on the secondary platform and is preferably augmented by data processing in the one or more workstations.

The entire disclosures of all applications, patents, and publications, cited herein, including the proposal by the Coleman Research Corporation entitled "Volume II—Technical Proposal, Research Area 6, Characterization, Maturity Level III—Sub-Scale Major Subsystems," Solicitation No. DE-RA21-92MC29249 (Sep. 16, 1992), are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An apparatus for mapping and characterizing the chemical composition of a surface, which comprises:
    a primary platform upon which is supported an optical vision system which topographically maps surfaces within a target volume by directing a source light beam through the target volume, receiving the reflected source light beam from a point on a surface within the target volume, and analyzing the reflected source light beam to provide a locus for a topographical map, said optical vision system having means for scanning the source light beam through multiple points within the target volume;
    a secondary platform upon which is supported a multisensor head and means for manipulating the position of the multisensor head over the mapped surface within the target volume, the multisensor head comprising at least one analytical probe connected to a remote detector which samples portions of the mapped surfaces within the target volume for chemical analysis;
    a remote detector which, together with an analytical probe, performs chemical analysis in situ on the sample portions of the mapped surfaces within the target volume; and one or more workstations with data processing means which:

controls the means for scanning the source light beam through multiple points within the target volume, monitors the position of the multisensor head within the target volume from input by the optical vision system, controls the means for manipulating the position of the multisensor head over the mapped surfaces within the target volume, correlates data from the remote detector and analytical probe with data from the optical vision system, and reports the results of the chemical analysis of the sample portions and the locations of the sample portions on the mapped surfaces.

2. The apparatus of claim 1, wherein the workstation is remote from the primary and secondary platforms.

3. The apparatus of claim 2, wherein the primary and secondary platforms are mobile, and each includes a transport vehicle remotely controlled by the workstation.

4. The apparatus of claim 1, wherein the workstation additionally archives the results of chemical analyses of the sample portions and the locations of the sample portions on the mapped surfaces.

5. The apparatus of claim 1, wherein the optical vision system has a range error of less than 1 mm at a range of 5 m.

6. The apparatus of claim 5, wherein the optical vision system has a position error of less than 1 mm at a range of 30 m.

7. The apparatus of claim 1, wherein the results of the chemical analysis of the sample portions and the locations of the sample portions on the mapped surfaces are reported on-site in real time.

8. The apparatus of claim 1, wherein the multisensor head comprises analytical probes for gas chromatography/mass spectrometry, molecular vibrational spectrometry, or combinations thereof.

9. The apparatus of claim 8, wherein the analytical probes are connected to remote detectors adapted to detect polychlorinated biphenyls (PCB's) in parts per billion.

10. The apparatus of claim 1, wherein the multisensor head includes a surface proximity sensor which detects the proximity of the multisensor head from the mapped surfaces within the target volume and/or a light sensor which detects the light emitted from the optical vision system or reflector means for reflecting the source light beam emitted from the optical vision system.

11. An apparatus for mapping and characterizing the chemical composition of a surface, which comprises:

a primary mobile platform comprising a remotely controlled transport vehicle upon which is supported a frequency-modulated coherent laser radar 3D mapper system to topographically map surfaces within a target volume, said frequency-modulated coherent laser radar 3D mapper system having means for scanning a laser beam through multiple points within the target volume;

a secondary mobile platform comprising a remotely controlled transport vehicle upon which is supported a multisensor head and means for manipulating the position of the multisensor head over the mapped surfaces within the target volume, said multisensor head comprising one or more analytical probes connected to a remote detector which samples portions of the mapped surfaces within the target volume for chemical analysis;

one or more remote detectors which, together with an analytical probe, perform chemical analysis in situ on the sample portions of the mapped surfaces within the target volume; and one or more workstations with data processing means remote from the primary and secondary platforms, which:

controls the transport vehicles of the primary and secondary platforms, controls the means for scanning the laser through multiple points within the target volume, monitors the position of the multisensor head within the target volume from input by the frequency-modulated coherent laser 3D mapper system, controls the means for manipulating the position of the multisensor head over the mapped surfaces within the target volume, correlates data from the one or more remote detectors and analytical probes with data from the frequency-modulated coherent laser radar 3D mapper system, and reports and archives the results of the chemical analysis of the sample portions and the locations of the sample portions on the mapped surfaces.

12. The apparatus of claim 11, wherein the frequency-modulated coherent laser radar 3D mapper system has a range error of less than 5 mm at a range of 5 m.

13. The apparatus of claim 11, wherein the frequency-modulated coherent laser radar 3D mapper system has a position error of less than 1 mm at a range of 40 m.

14. The apparatus of claim 11, wherein the frequency-modulated coherent laser radar 3D mapper system utilizes fiber optics to provide a local oscillator beam for comparison to a reflected light beam in topographically mapping surfaces within a target volume.

15. The apparatus of claim 11, wherein the multisensor head includes a surface proximity sensor which detects the proximity of the multisensor head from the mapped surfaces within the target volume and/or a light sensor to detect the laser beam or reflector means for reflecting the laser beam emitted by the frequency-modulated coherent laser radar mapping system.

16. The apparatus of claim 11, which includes more than one primary mobile platform and more than one secondary mobile platform controlled by one or more workstations.

17. The apparatus of claim 11, wherein the frequency-modulated coherent laser radar 3D mapper system makes more than 1000 measurements/second as the laser is scanned through the target volume.

18. The apparatus of claim 11, wherein the probe can be repositioned to take samples within time intervals of less than 10 seconds.

19. The apparatus of claim 11, wherein the analytical probes sample portions of the mapped surfaces having an area of 10 $cm^2$ or less and a depth of 0.5–1 mm.

20. The apparatus of claim 11, wherein the results of the chemical analysis of the sample portions and the locations of the sample portions on the mapped surfaces are reported on-site in real time.

21. The apparatus of claim 11, wherein the multisensor head comprises analytical probes for gas chromatography/mass spectrometry, molecular vibrational spectrometry, or combinations thereof.

22. The apparatus of claim 21, wherein the analytical probes are connected to remote detectors which detect polychlorinated biphenyls (PCB's) in parts per billion.

23. The apparatus of claim 22, wherein chemical analysis of sample portions by the probe/detector combination is obtained in less than 60 seconds.

24. The apparatus of claim 22, wherein chemical analysis of sample portions by the probe/detector combination is obtained in less than 30 seconds.

25. The apparatus of claim 11, wherein the multisensor head contains an analytical probe for a remote, high speed gas chromatograph positioned on the mobile secondary platform wherein separation of selected vapors is accomplished within 100 seconds or less.

26. The apparatus of claim 25, wherein the high speed gas chromatograph is coupled to a time-of-flight mass spectrometer positioned on the mobile secondary platform.

27. The apparatus of claim 11, wherein the multisensor probe includes a detector for $\alpha$- and $\beta$-particles with energy resolution suitable to identify $U^{235}$, $U^{238}$, $Pu^{239}$, $Th^{230}$.

28. The apparatus of claim 11, wherein the multisensor head includes one or more fiber optic probes connected to remote detectors for one or more molecular vibrational spectrometers remote from the primary mobile platform and secondary mobile platform.

29. The apparatus of claim 28, wherein the molecular vibrational spectrometer performs a spectrophotometric technique independently selected from near-infrared Raman spectrometry and mid-infrared external reflecting spectrometry.

30. The apparatus of claim 28, which utilizes a molecular vibrational spectrometer which detects transformer oil within an inorganic matrix and identify asbestos and concrete, transite, synthetic polymers, wood, and metal.

31. An apparatus for mapping and characterizing the chemical composition of a surface, which comprises:
(a) one or more remotely controlled transport vehicles upon which is supported (i) a scanning coherent laser detection system which topographically maps surfaces within a target volume by scanning a laser beam through the target volume, receiving the reflected laser beam from points on a surface within the target volume, and analyzing the selected laser beam to provide loci for a topographical map; and (ii) a multisensor head attached to a robotic arm adapted to manipulate the position of the multisensor head over the mapped surfaces within the target volume, wherein the multisensor head comprises multiple analytical probes which sample portions of the mapped surfaces within the target volume for in situ chemical analysis by multiple remote detectors which comprise high speed gas chromatography coupled to a time-of-flight mass spectrometer and molecular vibrational spectrometer; and
(b) one or more workstations with data processing means remote from the one or more remotely controlled transport vehicles which:
controls the one or more transport vehicles,
controls the robotic arm which manipulates the position of the multisensor head over the mapped surfaces within the target volume,
monitors the position of the multisensor head within the target volume from input by the light sensor and the scanning coherent laser detection system,
correlates data from the one or more remote detectors and analytical probes with data from the scanning coherent laser detection system, and
reports the results of the chemical analysis and locations of the sample portions on the mapped surfaces.

32. The apparatus of claim 31, wherein the results of the chemical analysis of the sample portions and the locations of the sample portions on the mapped surfaces are reported on-site in real time.

33. The apparatus of claim 31, wherein chemical analysis of sample portions by the probe/detector combination is obtained in less than 60 seconds.

34. The apparatus of claim 31, wherein chemical analysis of sample portions by the probe/detector combination is obtained in less than 30 seconds.

35. The apparatus of claim 31, wherein the analytic probe for the remote high speed gas chromatograph vaporizes organic compounds from the sample portions and transports them to a collector/concentrator.

36. The apparatus of claim 31, wherein the molecular vibrational spectrometer performs a spectrophotometric technique independently selected from near-infrared Raman spectrometry and mid-infrared external reflecting spectrometry.

37. The apparatus of claim 31, which utilizes a molecular vibrational spectrometer to detect transformer oil within an inorganic matrix and identify asbestos and concrete, transite, synthetic polymers, wood, and metal.

38. The apparatus of claim 31, wherein the multisensor probe includes a detector for $\alpha$- and $\beta$-particles with energy resolution suitable to identify $U^{235}$, $U^{238}$, $Pu^{239}$, and $Th^{230}$.

* * * * *